(12) United States Patent
Cuddihy et al.

(10) Patent No.: US 10,159,410 B2
(45) Date of Patent: Dec. 25, 2018

(54) METHOD AND APPARATUS FOR BIOMETRIC DATA GATHERING AND DISSEMINATION

(71) Applicant: Ford Global Technologies, LLC, Dearborn, MI (US)

(72) Inventors: Mark A. Cuddihy, New Boston, MI (US); Manoharprasad K. Rao, Novi, MI (US); Jialiang Le, Canton, MI (US); Kwaku O. Prakah-Asante, Commerce Township, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 474 days.

(21) Appl. No.: 14/551,583

(22) Filed: Nov. 24, 2014

(65) Prior Publication Data

US 2016/0143531 A1    May 26, 2016

(51) Int. Cl.

| | |
|---|---|
| *G08C 19/22* | (2006.01) |
| *H04Q 9/00* | (2006.01) |
| *A61B 5/00* | (2006.01) |
| *B60K 28/02* | (2006.01) |
| *G06F 9/445* | (2018.01) |
| *G06F 19/00* | (2018.01) |
| *G16H 40/67* | (2018.01) |
| *B60R 21/00* | (2006.01) |

(Continued)

(52) U.S. Cl.
CPC .......... *A61B 5/0022* (2013.01); *A61B 5/7405* (2013.01); *A61B 5/747* (2013.01); *B60K 28/02* (2013.01); *G06F 9/4451* (2013.01); *G06F 19/00* (2013.01); *G16H 40/67* (2018.01); *A61B 5/02438* (2013.01); *A61B 2503/22* (2013.01); *B60R 2021/0027* (2013.01); *G08B 25/016* (2013.01)

(58) Field of Classification Search
CPC ....................... A61B 5/0022; B60R 2021/0027
USPC ..................................................... 340/870.07
See application file for complete search history.

(56) References Cited

U.S. PATENT DOCUMENTS

2002/0154006 A1* 10/2002 Murphy .............. B60R 21/0136
340/436
2008/0167757 A1*  7/2008 Kanevsky .............. G07C 5/085
701/1

(Continued)

OTHER PUBLICATIONS

Jason Hiner for Between the Lines, Ford to use wearables to improve health and safety in cars, http://www/zdnet.com/ford-to-use-wearables-to-improve-health, Jun. 27, 2014.

(Continued)

*Primary Examiner* — Tanmay Shah
(74) *Attorney, Agent, or Firm* — Jennifer Stec; Brooks Kushman P.C.

(57) ABSTRACT

A system includes a processor configured to determine that a vehicle accident has occurred. The processor is also configured to connect to a detected wearable device. The processor is additionally configured to request measured present biometric information from the wearable device, in response to the accident determination. Also, the processor is configured to receive measured present biometric information from the wearable device and relay the biometric information to a connected emergency operator.

5 Claims, 4 Drawing Sheets

(51) Int. Cl.
*A61B 5/024* (2006.01)
*G08B 25/01* (2006.01)

(56) References Cited

U.S. PATENT DOCUMENTS

| | | | |
|---|---|---|---|
| 2012/0068820 A1* | 3/2012 | Mollicone | G06F 21/00 |
| | | | 340/5.82 |
| 2014/0097957 A1* | 4/2014 | Breed | G08B 21/06 |
| | | | 340/576 |
| 2014/0143785 A1 | 5/2014 | Mistry et al. | |
| 2015/0084757 A1* | 3/2015 | Annibale | G08B 25/10 |
| | | | 340/436 |
| 2015/0161876 A1* | 6/2015 | Castillo | G08B 21/0446 |
| | | | 340/539.11 |
| 2015/0180943 A1* | 6/2015 | Cradick | G06F 3/0482 |
| | | | 715/747 |

OTHER PUBLICATIONS

Florian Schumacher, Wearables in the Automotive Industry, Wearable Technologies, http://wearable-technologies.com/2014/05/wearables-in-the-automotive-industry, May 16, 2014.

\* cited by examiner

METHOD AND APPARATUS FOR BIOMETRIC DATA GATHERING AND DISSEMINATION

TECHNICAL FIELD

The illustrative embodiments generally relate to a method and apparatus for biometric data gathering and dissemination.

BACKGROUND

With a wealth of information available to vehicle computing systems through connected, brought-in devices, vehicle original equipment manufacturers (OEM)s are constantly seeking ways to utilize the information to improve the driving experience. Playlists from mobile devices, occupant phone contact information, even instant alerts for an incoming text message are all being made available to occupants through a user interface.

Some in-vehicle systems even use occupant biometric information to track occupant health. In this case, the occupants themselves function as the brought-in device, carrying internal biometric information into a vehicle. Information can be extracted and utilized via installed in-vehicle biometric sensors such as heart rate sensors in a steering wheel or in a seat.

While the information gathered from such sensors is potentially useful for occupant health feedback and reporting during an accident, it costs a significant amount of money to install such sensors in a vehicle. Further, if the occupant is left in a position post-crash that leaves the steering wheel out of reach or the occupant is no longer in proper contact with the seat based sensor (or if the sensors are damaged), the system cannot gather present information, and must rely on previously collected information. First responders would, of course, prefer up-to-date information, since an indication that an occupant pulse was normal prior to a crash gives virtually no information about the current state of the occupant following the crash, and what kind of treatment may be needed.

SUMMARY

In a first illustrative embodiment, a system includes a processor configured to determine that a vehicle accident has occurred. The processor is also configured to connect to a detected wearable device. The processor is additionally configured to request measured present biometric information from the wearable device, in response to the accident determination. Also, the processor is configured to receive measured present biometric information from the wearable device and relay the biometric information to a connected emergency operator.

In a second illustrative embodiment, a system includes a processor configured to connect to a detected wearable device. The processor is also configured to retrieve a user-profile corresponding to a received wearable device identification. Further, the processor is configured to determine a user-location corresponding to the wearable device location and adjust a vehicle safety system based on information contained in the user profile.

In a third illustrative embodiment, a system includes a processor configured to connect to a detected wearable device, having biometric measuring capability. The processor is also configured to determine a biometric measurement threshold corresponding to an alert state. Further, the processor is configured to monitor biometric information received from the wearable device to determine if the threshold was exceeded and instruct alert provision when the threshold is exceeded.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
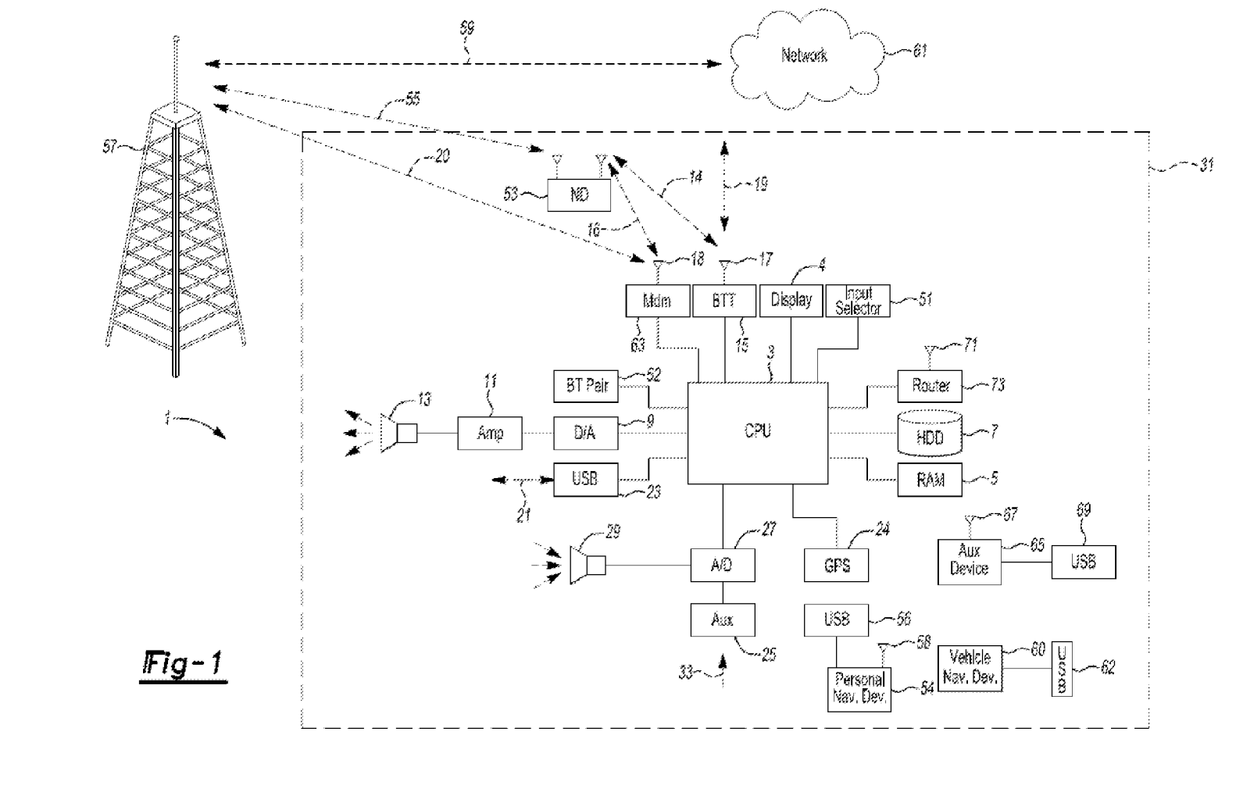
FIG. 1 shows an illustrative vehicle computing system.

FIG. 1 illustrates an example block topology for a vehicle based computing system 1 (VCS) for a vehicle 31. An example of such a vehicle-based computing system 1 is the SYNC system manufactured by THE FORD MOTOR COMPANY. A vehicle enabled with a vehicle-based computing system may contain a visual front end interface 4 located in the vehicle. The user may also be able to interact with the interface if it is provided, for example, with a touch sensitive screen. In another illustrative embodiment, the interaction occurs through, button presses, spoken dialog system with automatic speech recognition and speech synthesis.

In the illustrative embodiment 1 shown in FIG. 1, a processor 3 controls at least some portion of the operation of the vehicle-based computing system. Provided within the vehicle, the processor allows onboard processing of commands and routines. Further, the processor is connected to both non-persistent 5 and persistent storage 7. In this illustrative embodiment, the non-persistent storage is random access memory (RAM) and the persistent storage is a hard disk drive (HDD) or flash memory. In general, persistent (non-transitory) memory can include all forms of memory that maintain data when a computer or other device is powered down. These include, but are not limited to, HDDs, CDs, DVDs, magnetic tapes, solid state drives, portable USB drives and any other suitable form of persistent memory.

The processor is also provided with a number of different inputs allowing the user to interface with the processor. In this illustrative embodiment, a microphone 29, an auxiliary input 25 (for input 33), a USB input 23, a GPS input 24, screen 4, which may be a touchscreen display, and a BLUETOOTH input 15 are all provided. An input selector 51 is also provided, to allow a user to swap between various inputs. Input to both the microphone and the auxiliary connector is converted from analog to digital by a converter 27 before being passed to the processor. Although not shown, numerous of the vehicle components and auxiliary components in communication with the VCS may use a vehicle network (such as, but not limited to, a CAN bus) to pass data to and from the VCS (or components thereof).

Outputs to the system can include, but are not limited to, a visual display 4 and a speaker 13 or stereo system output. The speaker is connected to an amplifier 11 and receives its signal from the processor 3 through a digital-to-analog converter 9. Output can also be made to a remote BLUETOOTH device such as PND 54 or a USB device such as vehicle navigation device 60 along the bi-directional data streams shown at 19 and 21 respectively.

In one illustrative embodiment, the system 1 uses the BLUETOOTH transceiver 15 to communicate 17 with a user's nomadic device 53 (e.g., cell phone, smart phone, PDA, or any other device having wireless remote network connectivity). The nomadic device can then be used to communicate 59 with a network 61 outside the vehicle 31 through, for example, communication 55 with a cellular tower 57. In some embodiments, tower 57 may be a WiFi access point.

Exemplary communication between the nomadic device and the BLUETOOTH transceiver is represented by signal 14.

Pairing a nomadic device 53 and the BLUETOOTH transceiver 15 can be instructed through a button 52 or similar input. Accordingly, the CPU is instructed that the onboard BLUETOOTH transceiver will be paired with a BLUETOOTH transceiver in a nomadic device.

Data may be communicated between CPU 3 and network 61 utilizing, for example, a data-plan, data over voice, or DTMF tones associated with nomadic device 53. Alternatively, it may be desirable to include an onboard modem 63 having antenna 18 in order to communicate 16 data between CPU 3 and network 61 over the voice band. The nomadic device 53 can then be used to communicate 59 with a network 61 outside the vehicle 31 through, for example, communication 55 with a cellular tower 57. In some embodiments, the modem 63 may establish communication 20 with the tower 57 for communicating with network 61. As a non-limiting example, modem 63 may be a USB cellular modem and communication 20 may be cellular communication.

In one illustrative embodiment, the processor is provided with an operating system including an API to communicate with modem application software. The modem application software may access an embedded module or firmware on the BLUETOOTH transceiver to complete wireless communication with a remote BLUETOOTH transceiver (such as that found in a nomadic device). Bluetooth is a subset of the IEEE 802 PAN (personal area network) protocols. IEEE 802 LAN (local area network) protocols include WiFi and have considerable cross-functionality with IEEE 802 PAN. Both are suitable for wireless communication within a vehicle. Another communication means that can be used in this realm is free-space optical communication (such as IrDA) and non-standardized consumer IR protocols.

In another embodiment, nomadic device 53 includes a modem for voice band or broadband data communication. In the data-over-voice embodiment, a technique known as frequency division multiplexing may be implemented when the owner of the nomadic device can talk over the device while data is being transferred. At other times, when the owner is not using the device, the data transfer can use the whole bandwidth (300 Hz to 3.4 kHz in one example). While frequency division multiplexing may be common for analog cellular communication between the vehicle and the internet, and is still used, it has been largely replaced by hybrids of Code Domain Multiple Access (CDMA), Time Domain Multiple Access (TDMA), Space-Domain Multiple Access (SDMA) for digital cellular communication. These are all ITU IMT-2000 (3G) compliant standards and offer data rates up to 2 mbs for stationary or walking users and 385 kbs for users in a moving vehicle. 3G standards are now being replaced by IMT-Advanced (4G) which offers 100 mbs for users in a vehicle and 1 gbs for stationary users. If the user has a data-plan associated with the nomadic device, it is possible that the data-plan allows for broad-band transmission and the system could use a much wider bandwidth (speeding up data transfer). In still another embodiment, nomadic device 53 is replaced with a cellular communication device (not shown) that is installed to vehicle 31. In yet another embodiment, the ND 53 may be a wireless local area network (LAN) device capable of communication over, for example (and without limitation), an 802.11g network (i.e., WiFi) or a WiMax network.

In one embodiment, incoming data can be passed through the nomadic device via a data-over-voice or data-plan, through the onboard BLUETOOTH transceiver and into the vehicle's internal processor 3. In the case of certain temporary data, for example, the data can be stored on the HDD or other storage media 7 until such time as the data is no longer needed.

Additional sources that may interface with the vehicle include a personal navigation device 54, having, for example, a USB connection 56 and/or an antenna 58, a vehicle navigation device 60 having a USB 62 or other connection, an onboard GPS device 24, or remote navigation system (not shown) having connectivity to network 61. USB is one of a class of serial networking protocols. IEEE 1394 (FireWire™ (Apple), i.LINK™ (Sony), and Lynx™ (Texas Instruments)), EIA (Electronics Industry Association) serial protocols, IEEE 1284 (Centronics Port), S/PDIF (Sony/Philips Digital Interconnect Format) and USB-IF (USB Implementers Forum) form the backbone of the device-device serial standards. Most of the protocols can be implemented for either electrical or optical communication.

Further, the CPU could be in communication with a variety of other auxiliary devices 65. These devices can be connected through a wireless 67 or wired 69 connection. Auxiliary device 65 may include, but are not limited to, personal media players, wireless health devices, portable computers, and the like.

Also, or alternatively, the CPU could be connected to a vehicle based wireless router 73, using for example a WiFi (IEEE 803.11) 71 transceiver. This could allow the CPU to connect to remote networks in range of the local router 73.

In addition to having exemplary processes executed by a vehicle computing system located in a vehicle, in certain embodiments, the exemplary processes may be executed by a computing system in communication with a vehicle computing system. Such a system may include, but is not limited to, a wireless device (e.g., and without limitation, a mobile phone) or a remote computing system (e.g., and without limitation, a server) connected through the wireless device. Collectively, such systems may be referred to as vehicle associated computing systems (VACS). In certain embodiments particular components of the VACS may perform particular portions of a process depending on the particular implementation of the system. By way of example and not limitation, if a process has a step of sending or receiving information with a paired wireless device, then it is likely that the wireless device is not performing that portion of the process, since the wireless device would not "send and receive" information with itself. One of ordinary skill in the art will understand when it is inappropriate to apply a particular computing system to a given solution.

In each of the illustrative embodiments discussed herein, an exemplary, non-limiting example of a process performable by a computing system is shown. With respect to each process, it is possible for the computing system executing the process to become, for the limited purpose of executing the process, configured as a special purpose processor to perform the process. All processes need not be performed in their entirety, and are understood to be examples of types of processes that may be performed to achieve elements of the invention. Additional steps may be added or removed from the exemplary processes as desired.

The illustrative embodiments present exemplary systems and methods for gathering user biometric data, specifically from user wearable devices. While medical devices with wireless connection capability have existed for some time, these devices cost thousands, tens of thousands, or even hundreds of thousands of dollars. Further, each device is typically designed to gather a specific type of data with a high degree of accuracy.

At the same time, user mobile devices have long been capable of storing a basic user medical profile, which can give at least an accounting of user medical data determined at the time of input.

If a vehicle system were to obtain useful, medical information from brought in medical devices and a user mobile device, several difficulties may be encountered. First, the medical device could be extremely expensive, which would likely limit the use to a fraction of a percent of drivers/occupants.

Also, each device typically only gathers one type or one category of data. Accordingly, communication may have to be made with a plurality of devices to gather all useful data. Even this would not be sufficient, as the brought-in medical devices typically do not store a user health profile, and further connection would have to be made with, for example, a mobile device in order to obtain a user medical profile (including, for example, height and weight information).

Gathering user medical information from a mobile device also suffers from a potential serious drawback, namely, that the mobile device is more subjected to being loaned out and/or left behind in a vehicle. If a driver borrowed his wife's phone, and a child left a phone in the vehicle, then information gathered from these devices would not be suitable to tune vehicle systems to the current driver, because the driver is neither the wife or child. Further, information sent to first responders would result in two false positive identifications of vehicle occupants, and a failure to identify the actual vehicle occupant, which could confuse responders and delay medical treatment.

The illustrative embodiments contemplate using a new type of mobile device, which will be called a wearable device and is distinguished from a typical mobile device in that it is physically worn by the user. This device can be provided with rudimentary biometric sensing (such as heartrate sensing, for example) and can also be used to store a user medical profile. Because such devices are likely to be mass-produced, it is far more reasonable for an automotive manufacturer to provide for communication with such devices, and the vehicle computing system can obtain desired information with only a single connection.

Further, people are far less likely to loan out a watch or glasses (two known types of wearables, although other wearables (rings, necklaces, etc.) are also contemplated) than a phone. Thus, connection with such a device is more likely to accurately present a profile of the device owner. Further, since the device can presumably record limited biometrics, previous biometrics can be stored in a profile and compared to current biometrics to further increase the likelihood of a match (i.e., a successful identification of an actual occupant through device recognition).

Finally, the wearable device is more likely (especially in the case of a watch or jewelry) to remain in contact with a user and in position following an accident, than relying on the user remaining in an appropriate location to communicate with in-vehicle biometric sensors. The device also does not require active steps by the user (such as grasping a steering wheel outfitted with pulse sensors) in order to record information.

Figure 2:
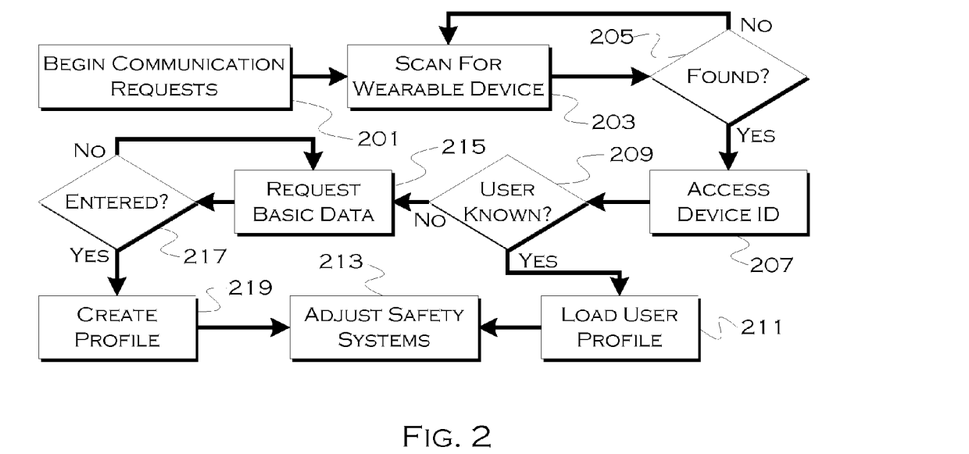
FIG. 2 shows an illustrative example of a vehicle system data retrieval and adjustment process.

FIG. 2 shows an illustrative example of a vehicle system data retrieval and adjustment process. With respect to the illustrative embodiments described in this figure, it is noted that a general purpose processor may be temporarily enabled as a special purpose processor for the purpose of executing some or all of the exemplary methods shown herein. When executing code providing instructions to perform some or all steps of the method, the processor may be temporarily repurposed as a special purpose processor, until such time as the method is completed. In another example, to the extent appropriate, firmware acting in accordance with a preconfigured processor may cause the processor to act as a special purpose processor provided for the purpose of performing the method or some reasonable variation thereof.

In this illustrative embodiment, once user data has been retrieved from the device, it can be used to adjust vehicle safety systems to better protect the user in the event of an accident. Further, if the information cannot be retrieved, a simple query can be used to establish a basic profile corresponding to the device.

At some point following vehicle activation (if the process is running on a vehicle computer, for example), the process can begin sending out connection requests to wearable devices in a vehicle 201. Since devices communicating with the vehicle are typically capable of identifying themselves, the system can "know" which communicating devices are wearables and which are mobile devices, tablets, personal computers, music players, etc. The process can scan for any available wearable devices 203 among available connectable devices present in the vehicle. Until a device is found (or, for example, until a reasonable timeout occurs) 205, the process can continue searching for present wearable devices.

Once a suitable wearable device has been found, the process can proceed to access a device ID 207, which can be used to identify the device and a corresponding known device owner. If the system has a profile saved or known for the owner 209, the local profile can be loaded 211 and used to adjust vehicle airbags, seat-belt restraint tensions, etc. 213, based on the device owner's known height, weight, etc.

On the other hand, if there is no profile saved for the user 209, the process can request some basic data needed to perform the preferred safety adjustments 215. This request can include any data suitable for storage and usable to adjust the vehicle systems. The process can also store both the user profile and the user personal data directly to the wearable itself, if a user is concerned about this data being stored or saved on a local vehicle computer. Once the requisite medical data has been entered 217, the process can create a user profile including the data and corresponding to the wearable device 219. In this manner, once the device is next detected, the process can access the appropriate user profile.

Biometric data provided by the device can also be recorded over a period of time and/or at intervals, and can be used as a verification step if the device is later detected. User biometric data presently read by the device can be compared to stored previous biometric profiles to ensure a greater degree of accuracy when identifying the presence of a user to be used as a basis for safety system adjustment.

Figure 3:
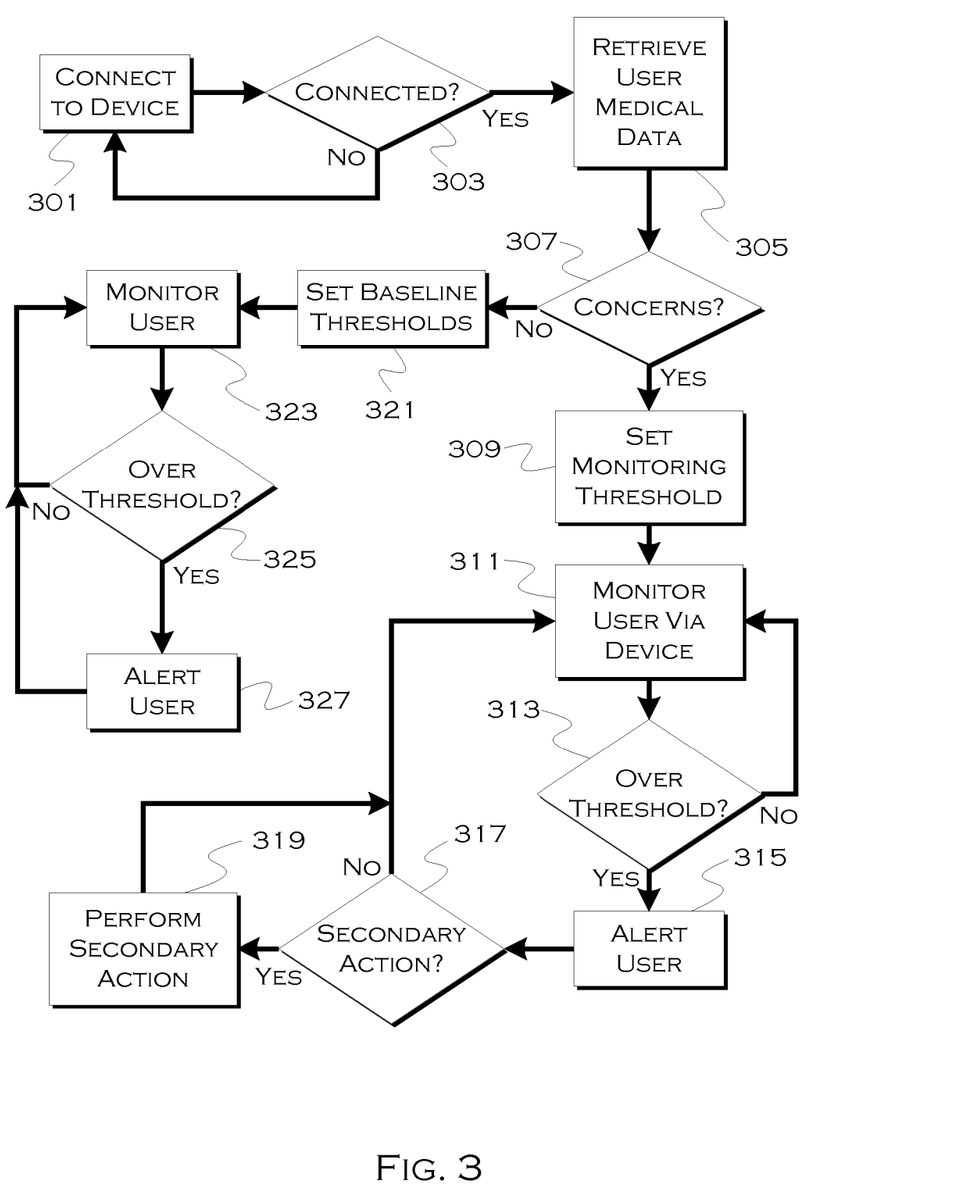
FIG. 3 shows an illustrative example of a user monitoring process.

FIG. 3 shows an illustrative example of a user monitoring process. With respect to the illustrative embodiments described in this figure, it is noted that a general purpose processor may be temporarily enabled as a special purpose processor for the purpose of executing some or all of the exemplary methods shown herein. When executing code providing instructions to perform some or all steps of the method, the processor may be temporarily repurposed as a special purpose processor, until such time as the method is completed. In another example, to the extent appropriate, firmware acting in accordance with a preconfigured processor may cause the processor to act as a special purpose processor provided for the purpose of performing the method or some reasonable variation thereof.

In this illustrative embodiment, the vehicle computer can monitor a user device to determine if a measured biometric exceeds a threshold range. Again in this example, the process connects to a user wearable device, capable of measuring at least one biometric value 301. Once connected 303, the process can retrieve a user medical profile 305. This profile can be received from a cloud-source, retrieved from local storage or even stored on the device itself. The profile may be rudimentary in nature, but at a minimum could include recorded biometric readings from previous communications with the wearable device. Also, it is possible that users with certain medical conditions may have thresholds set in the profile above which a biometric reading should not rise (e.g., a person with a heart condition may not want their heart rate to rise above a certain point).

If there are any specific medical thresholds set, relating to any user conditions 307, the process can set a monitoring threshold in the vehicle 309 and monitor a corresponding biometric through the wearable device 311. If, at any time, the reading rises over (or under) the threshold 313, the process can utilize a vehicle system to provide an alert to the user, or, for example, can instruct a user alert through the wearable device, such as haptic feedback 315. Again, since these devices are typically worn against the skin, haptic alerts are more likely to be sensed than from a mobile device such as a phone, carried in a pocket and possible set elsewhere in a vehicle. The nature of haptic feedback is also such that, regardless of vehicle noise (e.g., kids yelling) and driver attention on the road (e.g., high traffic), the alert is unlikely to be missed. Of course, as noted, in-vehicle systems such as audible outputs and displays can also be used to provide an alert, and, for a critical medical condition, multiple sources may be used to provide the alert to ensure that the alert is not overlooked.

The vehicle system can also provide an option for a secondary action 317, such as, but not limited to, moving the vehicle to the side of the road, calling emergency services, routing to the nearest pharmacy or doctor, or other suitable action. If the occupant elects a secondary action associated with the warning, the process will call the appropriate module to perform the action 319, otherwise, the monitoring can continue.

If there is no specific medical threshold for an alert condition pre-set in the medical data, baseline thresholds (based on generic user information for similar users, gathered user data, user set thresholds, etc.) can be set for monitoring 321. In one example, the process will can set an upper and lower threshold based on previously observed data (discarding outliers, for example) and use that as a baseline for providing user alerts. Again, the process can monitor the user 323 through the wearable device, and if the monitored values are over the threshold, the process can alert the user.

Figure 4:
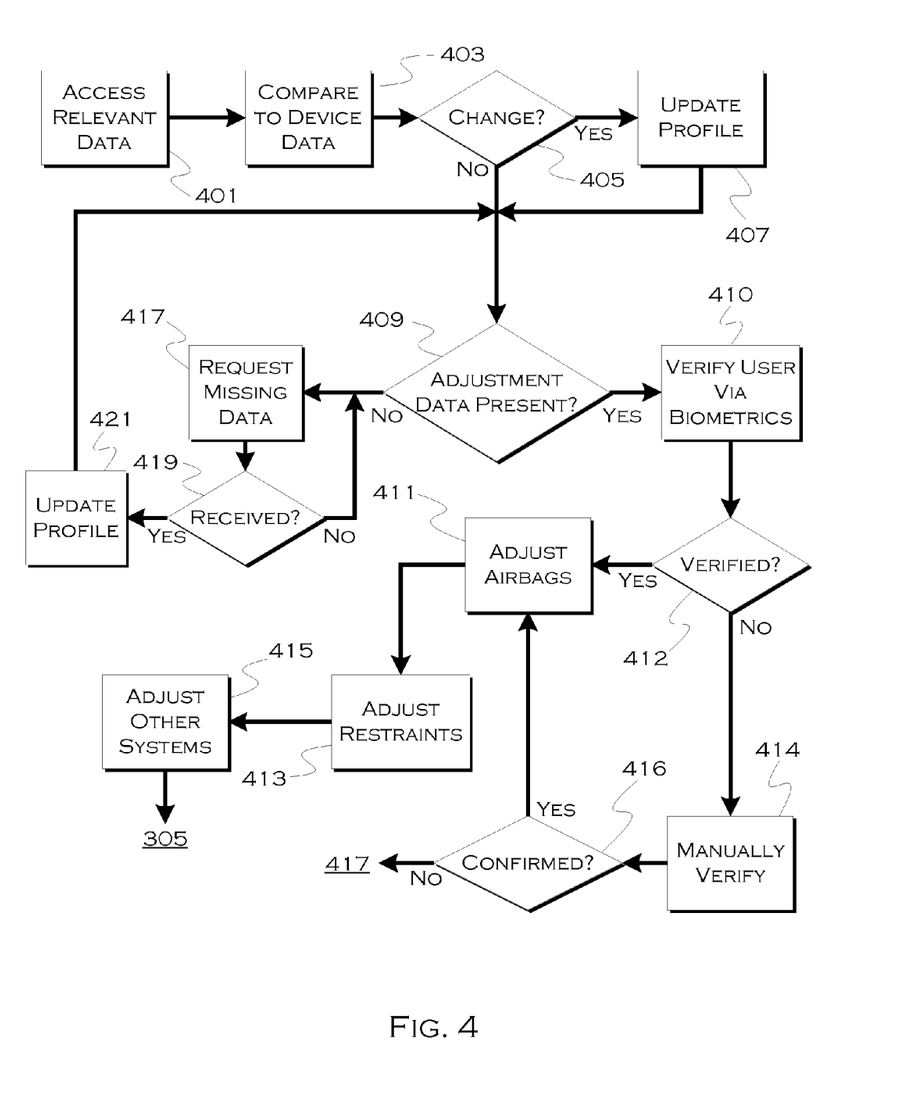
FIG. 4 shows an illustrative example of a system adjustment process.

FIG. 4 shows an illustrative example of a system adjustment process. With respect to the illustrative embodiments described in this figure, it is noted that a general purpose processor may be temporarily enabled as a special purpose processor for the purpose of executing some or all of the exemplary methods shown herein. When executing code providing instructions to perform some or all steps of the method, the processor may be temporarily repurposed as a special purpose processor, until such time as the method is completed. In another example, to the extent appropriate, firmware acting in accordance with a preconfigured processor may cause the processor to act as a special purpose processor provided for the purpose of performing the method or some reasonable variation thereof.

In this illustrative example, the process will adjust vehicle safety systems based on user presence detected through wearable devices so that optimal safety can be achieved. Once a wearable device has been connected and a user identity has been established, in this example, the process accesses a user profile (containing the information usable to adjust the safety systems, such as, but not limited to, height and weight) stored off of the wearable device 401. This data is then compared to data stored on the wearable device (if any), in case, for example, data has changed. Alternatively, the accessed user profile may be stored on the wearable device and then no comparison may be needed.

If there is a change in any of the data (i.e., the compared data does not match) 405, the process can update the stored user profile to reflect the changes in data 407. The process then determines if the data needed for making safety system adjustments is present 409. Some users may not want to share weight data, for example, so only systems that can be adjusted based on shared data may be adjusted. It is not necessary to gather all possible data for all system adjustments in order to adjust the systems that correspond to data the user is willing to share.

If the needed data (some or all) is not present in the profile 409, the process may request any missing data 417 (a time limit may be set for this step and if the adjustment data is not provided within this time limit, the system may use vehicle set default values for adjusting the vehicle systems such as safety systems). At this time, for example, the user can elect not to share certain data, and these preferences can be saved with respect to the profile so that the process does not continue to ask for data the user does not want to share. Once the missing data is received (or denied) 419, the process can update the user profile 421. Adjustment of the safety systems can then proceed.

In this example, as a further check to ensure the device corresponds to a user present in the vehicle, the process may seek to verify the user using biometric data gatherable by the wearable device 410. Assuming that some biometric data has been stored previously, currently gathered data can be compared to stored data to verify 412 the correspondence of device and user (and thus verify the user's presence). If there is no stored data, or the measured data is outside the verification range or does not match a verification value, the process may manually verify the user 414 by asking if User N is present in the vehicle, for example. Once this is confirmed 416, the process can proceed with adjustment. If the user cannot be confirmed, the process may ask for data relating to the user that is present 417 before adjusting the systems.

Since airbags and safety belts are deployed with respect to user positions in a vehicle, it is also useful to know the location of users before making adjustments. Known techniques for determining user locations based on wireless device identification can be used to determine location for any user identified by a wearable device. Additionally, drivers can be verified based on measuring, for example, movement corresponding to steering wheel movement in a wearable device worn on the hand or wrist. A wearable on the head can be used to verify a user location based on what is seen by the device camera (if provided).

While some of the techniques for user verification diminish the usefulness of the increased likelihood of proper identification based on the notion that wearable devices are more likely only used by a single person, the nature of the wearables still increases the value of the system when, for example, an accident occurs. That is, even if mobile devices such as phones could be used to determine occupancy (which would be subsequently verified) and even if the mobile devices provided user medical profiles, the mobile devices would be of little use in gathering occupant biometrics in the event of an accident. More is discussed on this point in relation to FIG. 5.

Once user locations are known or accurately guessed, airbag adjustments 411, restraint adjustments 413 and any other suitable vehicle system (safety or otherwise) adjustments 415 can be made.

Figure 5:
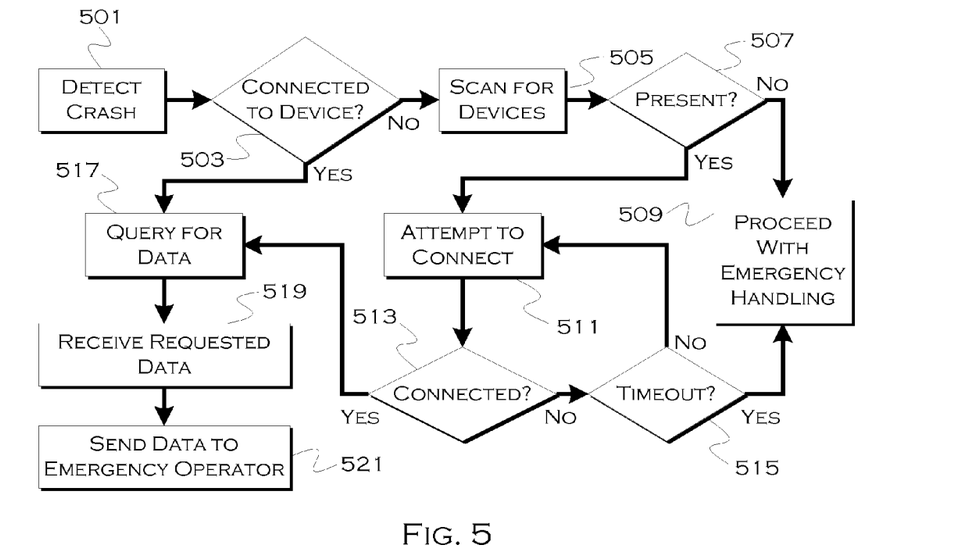
FIG. 5 shows an illustrative example of a post-crash data gathering process.

FIG. 5 shows an illustrative example of a post-crash data gathering process. With respect to the illustrative embodiments described in this figure, it is noted that a general purpose processor may be temporarily enabled as a special purpose processor for the purpose of executing some or all of the exemplary methods shown herein. When executing code providing instructions to perform some or all steps of the method, the processor may be temporarily repurposed as a special purpose processor, until such time as the method is completed. In another example, to the extent appropriate, firmware acting in accordance with a preconfigured processor may cause the processor to act as a special purpose processor provided for the purpose of performing the method or some reasonable variation thereof.

In this illustrative example, data relating to biometrics measureable by a wearable device will be gathered in a post-crash environment. As previously noted, because the wearable moves with a user, it is more likely to be in proper location for data gathering following an accident than an embedded vehicle system. And, since the device is typically in direct contact with the user, the device can be used to measure appropriate, available biometrics. Further, since these devices typically also have haptic and audible feedback, the device can be sent a series of signals to, for example, wake up a user if the user is, for example, believed to be unconscious based on measured biometric data (e.g., low heart rate). Again, as the device is typically worn against the skin, there is less likelihood of clothing interfering with, for example, a haptic signal.

In this example, the process detects a vehicle accident using known techniques 501. Once the accident is detected, the process (for each wearable device present, for example), determines if a connection is established with the device 503. If there is no connection, the process may scan to determine if any wearable devices are present and available 505.

If there is at least one device present and available for connection 507, the process may attempt to connect to the device 511, otherwise, the process can proceed with standard emergency situation handling 509. Until the device is connected 513 or a timeout occurs 515, the process may continue to attempt to connect. Once a connection is established, or if a connection to one or more devices was previously established, the process may query the device for data representing device-measurable biometrics 517. This can be done for each wearable device present in the vehicle, to obtain as accurate a picture as possible for provision to first responders. Depending on device detection techniques, wearable devices can also be used to provide present occupant location in a vehicle as well (indicating, for example, if an occupant is still in the vehicle, was thrown from the vehicle, was moved to a different part of the vehicle, etc. This is more reliable for wearable devices than for mobile devices which may have been set down elsewhere in the vehicle. To the extent that a wearable device includes biometric measuring capability, a quick reading can also determine if the device is still worn or not, which can then be used to determine the accurateness of any location-type information obtainable about the device (i.e., if there are no readings, the device may not be with the user, but if readings are obtainable, the device is likely worn, thus the device location is likely the user location).

Once any requested data (biometric, location, etc) has been received and/or determined 519, the process can send the appropriate data to an emergency operator 521. For example, the process could send user heart rate information and a notification that the user (based on device location) appears to be likely thrown from the vehicle. Also, at this time, the biometrics can be used to detect for certain states, such as, for example, unconsciousness. If the user is unconscious, the process can send a signal to the device to have the device haptically and/or audibly attempt to wake a user. If the user is thrown from the vehicle, and cannot hear a vehicle alert, a device moving with the user is more likely to have success in waking the user from an unconscious state.

In another embodiment, the device can attempt to determine if the user is conscious by providing stimuli, such as a request to interface with the device. If the user does not respond to the request, the device may attempt to wake the user through the aforementioned signal process. Again, since the device likely travels with the user, use of the device to provide such stimuli is likely to occur at the user location, where it is highly likely to be responded to (if possible).

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system comprising:
a processor configured to:
connect to a detected wearable device;
retrieve a user-profile corresponding to a received wearable device identification;
determine a user-location corresponding to the wearable device location; and
adjust a vehicle safety system based on information contained in the user profile.

2. The system of claim 1, wherein the safety system includes a seat-belt restraint tensioner.

3. The system of claim 1, wherein the safety system includes an airbag.

4. The system of claim 1, wherein the processor is further configured to:
   request present biometric information from the wearable device, measurable by the wearable device;
   receive the present biometric information;
   compare the present biometric information to saved biometric information previously received from the wearable device; and
   verify the identity of a user based on a correlation between the received present biometric information and the saved biometric information.

5. The system of claim 1, wherein the processor is further configured to:
   request input of information lacking in the user profile, needed to perform one or more vehicle safety system adjustments; and
   update the user-profile based on the received information.

* * * * *